(12) United States Patent
Elliott, Jr. et al.

(10) Patent No.: US 10,965,845 B2
(45) Date of Patent: *Mar. 30, 2021

(54) DURABLE FLEXIBLE CIRCUIT ASSEMBLY

(71) Applicant: Karl Storz Endovision, Inc., Charlton, MA (US)

(72) Inventors: John J. Elliott, Jr., Ashburnham, MA (US); David J. Guerra, Putnam, CT (US); Dashiell A. Birnkrant, Worcester, MA (US); James P. Barry, Charlton, MA (US)

(73) Assignee: KARL STORZ Endovision, Inc., Charlton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/425,612

(22) Filed: May 29, 2019

(65) Prior Publication Data

US 2019/0281196 A1 Sep. 12, 2019

Related U.S. Application Data

(63) Continuation of application No. 14/446,913, filed on Jul. 30, 2014, now Pat. No. 10,348,941.

(51) Int. Cl.
| | |
|---|---|
| *A61B 1/005* | (2006.01) |
| *A61B 1/05* | (2006.01) |
| *A61B 1/00* | (2006.01) |
| *H04N 5/225* | (2006.01) |
| *G02B 23/24* | (2006.01) |

(52) U.S. Cl.
CPC .......... *H04N 5/2252* (2013.01); *A61B 1/005* (2013.01); *A61B 1/0058* (2013.01); *A61B 1/00078* (2013.01); *A61B 1/00114* (2013.01); *A61B 1/05* (2013.01); *A61B 1/051* (2013.01); *A61B 1/0051* (2013.01); *A61B 1/0057* (2013.01); *G02B 23/2476* (2013.01); *G02B 23/2484* (2013.01)

(58) Field of Classification Search
CPC ........ A61B 1/005; A61B 1/0051–0053; A61B 1/0055–0058; A61B 1/00078; A61B 1/05; A61B 1/051; A61B 1/00114; G02B 23/2476; G02B 23/2484
See application file for complete search history.

*Primary Examiner* — Timothy J Neal
*Assistant Examiner* — William B Chou
(74) *Attorney, Agent, or Firm* — Michael J. Loi

(57) ABSTRACT

A flexible circuit assembly for an endoscope or borescope having an image sensor. The flexible circuit assembly has a flexible circuit with a first end, a second end, and a length between its first and second ends, the first end of the flexible circuit electrically connectable with the image sensor. A strengthening member is adjacent to the flexible circuit and along the length of the flexible circuit. An electrically insulated layer retains the strengthening member adjacent to the flexible circuit and encloses at least of portion of the strengthening member and the flexible circuit. The strengthening member may comprise a nitinol wire, and the nitinol wire may have a neutral position such that the nitinol wire returns to the neutral position after being articulated to a different position.

15 Claims, 1 Drawing Sheet

DURABLE FLEXIBLE CIRCUIT ASSEMBLY

CROSS-REFERENCE TO RELATED APPLICATIONS

This application is a continuation of and claims priority to U.S. Ser. No. 14/446,913, filed on Jul. 30, 2014 and entitled "Durable Flexible Circuit Assembly."

FIELD OF THE INVENTION

The present teachings relate generally to endoscopes and borescopes and, more particularly, to supporting a flexible circuit inside an articulating endoscope or borescope to reduce the risk of it breaking.

BACKGROUND OF THE INVENTION

As is known in the art, endoscopes are medical instruments used to examine an interior cavity of a body. They typically include a rigid or flexible shaft. The distal end of the endoscope shaft can have a light delivery system for illumination and a lens or image sensor to capture images. An endoscope may also have a channel to allow entry of medical instruments or manipulators.

In a similar manner, articulating borescopes used in industrial and/or scientific fields, may also include a rigid or flexible shaft, distal end light delivery system, and a lens and/or image sensor to capture images. Additionally, borescopes may also have a channel to allow use of instruments or manipulators. Herethroughout, the terms "endoscope" and "borescope" are used interchangeably.

In use, one end of the endoscope is inserted into a body so that images inside the body can be transmitted back to an eyepiece or other video display located outside the body. Accordingly, it is preferable to design an endoscope having a shaft with a small circumference because that will determine the size of the hole needed for inserting the endoscope into the body.

Flexible endoscopes, and even some rigid endoscopes, have an articulating section of the shaft that can bend. This permits a user to manipulate the endoscope to investigate different areas inside a body or to perform certain tasks, although not limited thereto. As a result, any component inside the endoscope shaft is preferably flexible.

For endoscopes that use an image sensor to capture images and transmit them back to a monitor, a number of electrical wires are required so that the image sensor is provided with power and communication connections. Traditionally, cable assemblies have been used to provide these connections, but such cable assemblies are expensive and difficult to manufacture. In addition, cable assemblies may lack strength to resist kinking and may break with repeated articulations of the endoscope.

Therefore, it would be beneficial to have a superior durable flexible circuit assembly for endoscopes and/or borescopes.

SUMMARY OF THE INVENTION

One objective of the present teachings is support the use of a flexible circuit in articulating endoscopes.

Another objective of the present teachings is to provide a flexible circuit assembly that can be manufactured more easily and less expensively.

Another objective of the present teachings is to provide a flexible circuit assembly having increased column strength and with reduced risk of kinking.

The objectives set forth herein as well as further and other objectives and advantages are addressed by the present embodiments, which illustrate solutions and advantages described below.

The flexible circuit assembly for an endoscope having an image sensor of the present embodiment includes, but is not limited to, a flexible circuit having a first end, a second end, and a length between its first and second ends, the first end of the flexible circuit electrically connectable with the image sensor, a strengthening member adjacent to the flexible circuit and along the length of the flexible circuit, and an electrically insulated layer retaining the strengthening member adjacent to the flexible circuit and enclosing at least of portion of the strengthening member and the flexible circuit.

In one embodiment, the strengthening member comprises a metal wire. The metal wire may be flat.

In one embodiment, the metal wire comprises a nitinol wire. The nitinol wire may have a neutral position, and the nitinol wire returns to the neutral position after being articulated to a different position.

In one embodiment, the strengthening member is located along less than a full length of the flexible circuit. The strengthening member may not extend to the first end of the flexible circuit.

Also disclosed is an endoscope comprising a shaft having inside the flexible circuit assembly according to the present teachings. The endoscope may be an articulating endoscope. A video display system may display images received from the image sensor.

Also disclosed is a method of manufacturing a flexible circuit assembly for an endoscope of the present embodiment. The endoscope has a working shaft. The flexible circuit assembly has a flexible circuit with a first end, a second end, and a length between its first and second ends, the first end of the flexible circuit electrically connectable with an image sensor, a strengthening member, and an electrically insulated layer. The method steps include, but are not limited to, positioning the strengthening member adjacent to the flexible circuit and along the length of the flexible circuit, enclosing at least of portion of the strengthening member and the flexible circuit with the electrically insulated layer to retain the strengthening member adjacent to the flexible circuit, and electrically connecting the flexible circuit to the image sensor.

In one embodiment, the method further comprises the step of inserting the flexible circuit assembly inside the working shaft of the endoscope. The flexible circuit assembly may be electrically connected to a video display system.

Also disclosed is an endoscope having a flexible circuit assembly and an image sensor that includes, but is not limited to, a flexible circuit having a first end, a second end, and a length between its first and second ends, the first end of the flexible circuit electrically connected to the image sensor, a nitinol wire adjacent to the flexible circuit and along the length of the flexible circuit, the nitinol wire having a neutral position such that the nitinol wire returns to the neutral position after being articulated to a different position, and an electrically insulated layer retaining the nitinol wire adjacent to the flexible circuit and enclosing at least of portion of the nitinol wire and the flexible circuit.

Other embodiments of the system and method are described in detail below and are also part of the present teachings.

For a better understanding of the present embodiments, together with other and further aspects thereof, reference is made to the accompanying drawings and detailed description, and its scope will be pointed out in the appended claims.

DETAILED DESCRIPTION OF THE INVENTION

Figure 1:
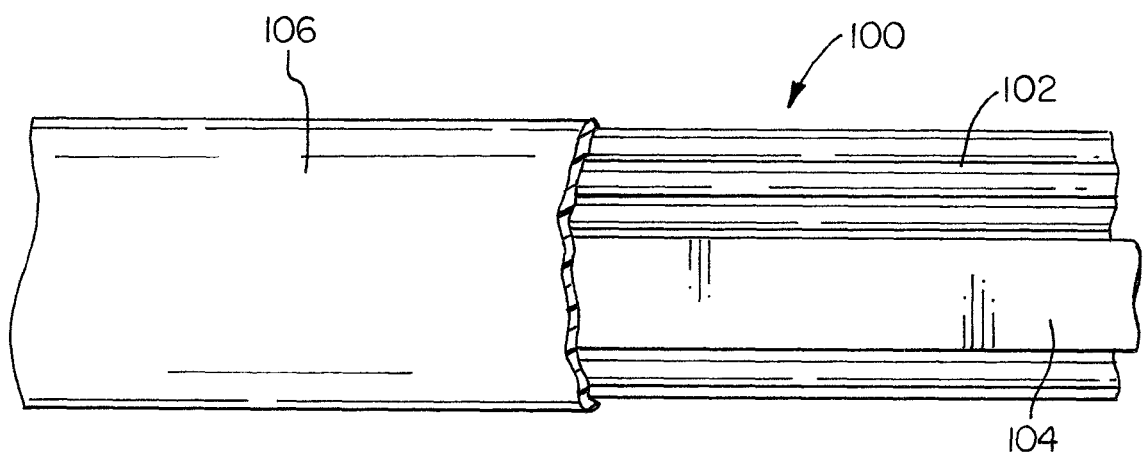
FIG. 1 shows one embodiment of the flexible circuit assembly for an endoscope according to the present teachings.

The present teachings are described more fully hereinafter with reference to the accompanying drawings, in which the present embodiments are shown. The following description is presented for illustrative purposes only and the present teachings should not be limited to these embodiments.

As is known to those skilled in the art, endoscopes that provide video imagery may have an electronic image sensor located at the distal tip of the endoscope. This image sensor may be wired to a supporting printed circuit board (PCB), for example, for power, to transmit clock signals, to transmit video signals, etc.

Typically, such wiring is accomplished by using a cable assembly that contains individual isolated wires. However, such cable assemblies are typically expensive. In addition, they may require highly skilled craftspersons to connect the image sensor and the PCB.

Many electronic image sensors have been packaged using chip scale packing (CSP) with ball grid arrays on the back side of the image sensor package. One convenient method to connect a ball grid array sensor to a supporting PCB is to use a flexible circuit (also referred to as "flex circuit"). A flex circuit is a type of thin PCB used for assembling electronic circuits by mounting electronic devices on a flexible plastic substrate. By using thin conductive and isolative layers, a flex circuit can be thin (e.g., <0.1 mm, etc.) and flexible, although not limited thereto, making it suitable for use in the shaft of an articulating endoscope.

Flex circuits may also be manufactured less expensively than traditional cable assemblies. For example, no manual labor may be required as all components, including the image sensor, supporting capacitors and resistors, connectors, etc., can be populated onto the flex circuit using automated PCB populating machines, although not limited thereto.

Flexible endoscopes, and even some rigid ones, have an articulating section of the shaft which can bend (e.g., +/−285 degrees, etc.). As the endoscope articulates, components inside the shaft may "piston" such that they move longitudinally along the axis of the working shaft. As a result, it may be preferable for components inside the shaft to be both flexible as well as have a certain amount of "column strength" to properly piston during articulation.

While flex circuits are flexible, they do not have a lot of column strength. If they get kinked (e.g., get a sharp bend, etc.) the kink may remain. As an endoscope articulates, the flex circuit may straighten and kink over and over again until components of the flex circuit eventually crack and break. Therefore, a way to give additional column strength to a flex circuit in an articulating endoscope is desirable.

In one embodiment according to the present teachings, a flexible circuit assembly for endoscopes comprises a flexible circuit, a strengthening member, and an insulated outer layer, although not limited thereto. So designed, the strengthening member may be used to support the flex circuit and reduce the risk of it breaking inside the endoscope.

The strengthening member may comprise a shape memory/elastic layer. In one embodiment, this may include a metal wire. The metal wire can be flat or round, although not limited thereto.

In one embodiment, the metal wire may comprise nitinol. Nitinol, also known as nickel titanium, is a metal alloy comprising nickel and titanium.

Nitinol exhibits properties preferable for the present teachings, including shape memory and elasticity, as would be appreciated by one skilled in the art. Shape memory is the ability to undergo deformation and then recover to an original, undeformed shape. Nitinol also exhibits more elasticity (e.g., 10-30 times, etc.) than ordinary metal.

In one embodiment, the strengthening member may be secured to the flex circuit using an adhesive. In another embodiment, nitinol wire can be secured onto the top of the flex circuit using the insulating layer. The insulating layer may accomplish a number of objectives. It may not only secure the nitinol wire in place but also isolate the nitinol wire and any electrical components on the flex circuit from the metal working shaft of the endoscope, although not limited thereto.

In one embodiment, the insulating layer may comprise heat shrink material. As would be appreciated by one skilled in the art, heat shrink is an extruded plastic that shrinks when heated. It may be used for electrical insulation as well as abrasion resistance and environmental protection, although not limited thereto.

By creating such an assembly, a flexible circuit assembly can be made that has a preferable amount of column strength so as to reduce the ability of the flex circuit to kink during articulations of the endoscope. The spring force of the strengthening member may also keep the flex circuit in "neutral" position to prevent any damage. With shape memory (e.g., nitinol), it may "spring" back to its original shape after it is bent.

Referring now to FIG. 1, shown is one embodiment of the flexible circuit assembly 100 for an endoscope according to the present teachings. As shown, the flexible circuit assembly 100 may comprise a flex circuit 102, a strengthening member 104 (e.g., nitinol wire, etc.), and an insulating layer 106, although not limited thereto.

In one embodiment, the strengthening member 104 may be formed of nitinol, which may be round or flat, although not limited thereto. The strengthening member 104 may be adjacent to the flex circuit 102 to strengthen the flex circuit 102 and reduce possible kinking. The strengthening member 104 may be secured in place by the insulating layer 106, although not limited thereto. In one embodiment, the insulating layer 106 may comprise heat shrinking, although not limited thereto.

In one embodiment, the strengthening member 104 may not be located along the entire length of the flex circuit 102. Instead, it may be positioned to support key areas. This allows some areas of the flex circuit 102, like the distal end with the image sensor 122 (shown in FIG. 2), to remain flexible and small. In addition, this may provide for more manufacturing options to keep the endoscope distal end small and short, although not limited thereto.

Figure 2:
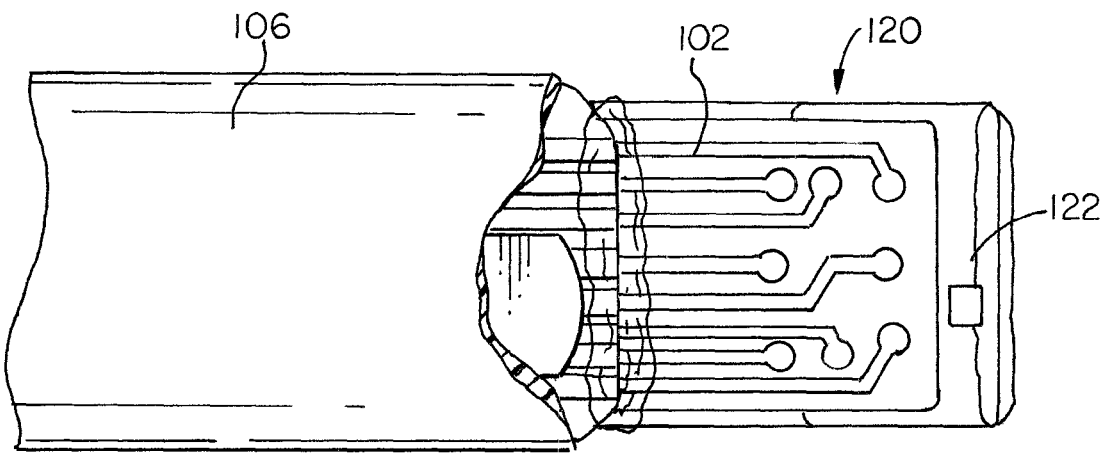
FIG. 2 shows the distal end of the flexible circuit assembly of FIG. 1.

Referring now to FIG. 2, shown is the distal end 120 of the flexible circuit assembly of FIG. 1. An image sensor 122 may be connected to the flex circuit 102, which may have a strengthening member 104 (shown in FIG. 1) and be enclosed by an insulating layer 106.

In use, the flexible circuit assembly 100 may be inserted into the working shaft of an endoscope. Images may be captured by the image sensor 122 and transmitted through the endoscope to a video display system (e.g., monitor, eyepiece, etc.), as would be appreciated by one skilled in the art.

The strengthening member 104 may be made from a number of different materials, as will be appreciated by one skilled in the art. For example, steel may be used. This may provide the desired column strength, although steel is stiffer than nitinol and it may take more force to articulate the assembly. In addition, steel lacks the shape memory feature of nitinol and may not "spring" back to its original shape. So, if a kink occurs using a steel wire, the kink may remain.

In one embodiment, the flexible circuit assembly may be manufactured where the insulating layer comprises the strengthening member by utilizing insulating layers. These layers may have various thicknesses to provide strength along the length of the flex circuit. This way it is possible to make the flex circuit more flexible at the distal end of the endoscope (e.g., thinner insulating layers), but more rigid along the length inside the working shaft (e.g., thicker insulating layers). In one embodiment, the insulating layers may comprise thicker polymer materials to provide adequate strength, although not limited thereto.

While the present teachings have been described above in terms of specific embodiments, it is to be understood that they are not limited to these disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. A flexible circuit assembly for a video imaging endoscope or borescope, comprising:
    an electronic image sensor arranged to capture video images;
    a flexible circuit having a first end, a second end, and a length between its first and second ends;
    the first end of the flexible circuit electrically connected with the electronic image sensor, such that the first end and the electronic image sensor can bend together with respect to the length along a portion of the flexible circuit excluding the electronic image sensor;
    a strengthening member adjacent to the flexible circuit and along the length of the flexible circuit, the strengthening member providing additional column strength to the flexible circuit and reducing kinking when the flexible circuit bends during articulation of the video imaging endoscope or borescope;
    an electrically insulated layer enclosing the strengthening member and the flexible circuit along the length of the flexible circuit;
    the flexible circuit assembly arranged to be inserted inside a working shaft of the video imaging endoscope or borescope.

2. The assembly of claim 1, wherein the electrically insulated layer extends from the first end to the second end of the flexible circuit.

3. The assembly of claim 1, wherein the electrically insulated layer comprises heat shrink material.

4. The assembly of claim 1, wherein the electrically insulated layer has varying thickness, such that it is thinner at the first end of the flexible circuit in order to provide more flexibility, and is thicker along the length of the flexible circuit to provide more strength.

5. The assembly of claim 1, wherein the strengthening member extends to the first end such that it is adjacent the image sensor.

6. The assembly of claim 1, wherein the strengthening member does not extend to the first end of the flexible circuit.

7. The assembly of claim 1, wherein the strengthening member comprises a metal wire.

8. The assembly of claim 7, wherein the metal wire is flat.

9. The assembly of claim 1, wherein the strengthening member comprises a nitinol wire that has a neutral position, and the nitinol wire returns to the neutral position after being articulated to a different position.

10. An endoscope or borescope, comprising a working shaft having inside the flexible circuit assembly of claim 1.

11. The endoscope or borescope of claim 10, further comprising a video display system displaying images received from the electronic image sensor.

12. A method of manufacturing a video imaging endoscope or borescope using a flexible circuit assembly, the flexible circuit assembly having:
    an electronic image sensor arranged to capture video images;
    a flexible circuit having a first end, a second end, and a length between its first and second ends;
    a strengthening member;
    an electrically insulated layer;
    the method comprising:
    electrically connecting the flexible circuit to the electronic image sensor, such that the first end and the electronic image sensor can bend together with respect to the length along a portion of the flexible circuit excluding the electronic image sensor;
    enclosing the strengthening member and the flexible circuit with the electrically insulated layer along the length of the flexible circuit;
    shrinking the electrically insulated layer around the strengthening member and the flexible circuit;
    arranging the flexible circuit assembly inside a working shaft of the video imaging endoscope or borescope;
    wherein the strengthening member provides additional column strength to the flexible circuit and reduces kinking when the flexible circuit bends during articulation of the video imaging endoscope or borescope.

13. The method of claim 12, wherein the electrically insulated layer extends from the first end to the second end of the flexible circuit.

14. The method of claim 12, further comprising electrically connecting the flexible circuit assembly to a video display system.

15. The method of claim 12, wherein the strengthening member comprises a nitinol wire that has a neutral position, and the nitinol wire returns to the neutral position after being articulated to a different position.

* * * * *